US007592011B2

(12) United States Patent
Hughes et al.

(10) Patent No.: US 7,592,011 B2
(45) Date of Patent: Sep. 22, 2009

(54) GENES AND PROTEINS, AND THEIR USE

(75) Inventors: Martin John Glenton Hughes, Berkshire (GB); Joseph David Santangelo, Berkshire (GB); Jonathan Douglas Lane, Berkshire (GB); Robert Feldman, Berkshire (GB); Joanne Christine Moore, Berkshire (GB); Richard James Dobson, Berkshire (GB); Paul Everest, Dumbartonshire (GB); Gordon Dougan, London (GB); Rebecca Kerry Wilson, London (GB)

(73) Assignee: Emergent Product Development UK Limited, Wokingham Berkshire (GB)

( * ) Notice: Subject to any disclaimer, the term of this patent is extended or adjusted under 35 U.S.C. 154(b) by 362 days.

(21) Appl. No.: 10/944,521

(22) Filed: Sep. 17, 2004

(65) Prior Publication Data
US 2005/0131210 A1 Jun. 16, 2005

Related U.S. Application Data

(63) Continuation of application No. 10/096,162, filed on Mar. 11, 2002, now Pat. No. 6,890,539, which is a continuation-in-part of application No. 09/868,352, filed as application No. PCT/GB99/04377 on Dec. 22, 1999, now Pat. No. 6,812,021.

(30) Foreign Application Priority Data

| Dec. 22, 1998 | (GB) | ................................. | 9828345.0 |
| Dec. 22, 1998 | (GB) | ................................. | 9828349.2 |
| Dec. 22, 1998 | (GB) | ................................. | 9828350.0 |
| Dec. 22, 1998 | (GB) | ................................. | 9828352.6 |
| Dec. 22, 1998 | (GB) | ................................. | 9828353.4 |
| Dec. 22, 1998 | (GB) | ................................. | 9828354.2 |
| Dec. 22, 1998 | (GB) | ................................. | 9828355.9 |
| Dec. 22, 1998 | (GB) | ................................. | 9828356.7 |
| Dec. 22, 1998 | (GB) | ................................. | 9828357.5 |
| Dec. 22, 1998 | (GB) | ................................. | 9828359.1 |
| Jan. 4, 1999 | (GB) | ................................. | 9900082.0 |
| Jan. 4, 1999 | (GB) | ................................. | 9900083.8 |
| Jan. 4, 1999 | (GB) | ................................. | 9900084.6 |
| Jan. 4, 1999 | (GB) | ................................. | 9900085.3 |
| Jan. 4, 1999 | (GB) | ................................. | 9900086.1 |
| Jan. 28, 1999 | (GB) | ................................. | 9901916.8 |
| Jan. 28, 1999 | (GB) | ................................. | 9901922.6 |
| Mar. 9, 2001 | (GB) | ................................. | 0105922.9 |

(51) Int. Cl.
*A61K 39/09* (2006.01)
*C07H 21/04* (2006.01)
*C12P 21/04* (2006.01)
*C12N 1/20* (2006.01)

(52) U.S. Cl. .............. 424/190.1; 424/184.1; 424/244.1; 536/23.7; 536/24.32; 530/300; 530/350; 435/69.1; 435/69.7; 435/252.3

(58) Field of Classification Search .............. 424/184.1; 435/69.1, 69.7; 530/300, 350; 536/23.7
See application file for complete search history.

(56) References Cited

U.S. PATENT DOCUMENTS

| 5,328,996 | A | 7/1994 | Boyle et al. |
| 5,807,978 | A * | 9/1998 | Kokolus et al. .............. 530/300 |
| 6,015,889 | A | 1/2000 | Lindahl et al. |
| 6,248,329 | B1 | 6/2001 | Chandrashekar et al. |
| 6,605,709 | B1 | 8/2003 | Breton |
| 6,699,703 | B1 | 3/2004 | Doucette-Stamm et al. |
| 6,800,744 | B1 | 10/2004 | Doucette-Stamm et al. |
| 6,812,021 | B1 | 11/2004 | Hughes et al. |
| 6,890,539 | B2 | 5/2005 | Hughes et al. |
| 7,196,164 | B2 | 3/2007 | Rosen et al. |
| 7,217,415 | B1 | 5/2007 | Hughes et al. |
| 2003/0104000 | A1 | 6/2003 | Hughes et al. |
| 2004/0044191 | A1 | 3/2004 | Fischer et al. |
| 2006/0104990 | A1 | 5/2006 | Hughes et al. |
| 2007/0053936 | A1 | 3/2007 | Doucette-Stamm et al. |

FOREIGN PATENT DOCUMENTS

| EP | 0 230 777 B1 | 8/1987 |
| EP | 0 913 476 A2 | 10/1997 |
| WO | WO 93/14198 A1 | 7/1993 |
| WO | WO 94/10317 A2 | 5/1994 |
| WO | WO 94/21685 A1 | 9/1994 |
| WO | WO 98/18931 A1 | 5/1998 |
| WO | WO 98/23631 A1 | 6/1998 |
| WO | WO 99/42588 A2 | 8/1999 |
| WO | WO 00/03744 A2 | 1/2000 |
| WO | WO 00/06736 A2 | 2/2000 |
| WO | WO 00/25728 A2 | 5/2000 |
| WO | WO 00/26397 A1 | 5/2000 |
| WO | WO 00/37646 A2 | 6/2000 |
| WO | WO 00/61621 A2 | 10/2000 |
| WO | WO 01/32882 A2 | 5/2001 |
| WO | WO 01/34809 A2 | 5/2001 |
| WO | WO 01/77335 A2 | 10/2001 |
| WO | WO 02/72623 A1 | 3/2002 |
| WO | WO 02/29103 A2 | 4/2002 |
| WO | WO 02/34771 A2 | 5/2002 |
| WO | WO 02/077021 A2 | 10/2002 |
| WO | WO 02/077183 A2 | 10/2002 |
| WO | WO 02/083855 A2 | 10/2002 |

(Continued)

OTHER PUBLICATIONS

Immunology, a short course by Benjamini et al, p. 4 only.*

(Continued)

*Primary Examiner*—Robert B Mondesi
*Assistant Examiner*—Padma V Baskar
(74) *Attorney, Agent, or Firm*—Sterne, Kesler, Goldstein & Fox P.L.L.C.

(57) ABSTRACT

A protein from Group B *Streptococcus* is shown to be an outer surface protein and is a useful target for antimicrobial therapy.

16 Claims, 1 Drawing Sheet

FOREIGN PATENT DOCUMENTS

| | | | |
|---|---|---|---|
| WO | WO 02/092818 A2 | 11/2002 |
| WO | WO 02/094868 A2 | 11/2002 |
| WO | WO 03/009869 A1 | 2/2003 |
| WO | WO 03/093306 A2 | 11/2003 |
| WO | WO 2004/030608 A2 | 4/2004 |
| WO | WO 2004/041157 A2 | 5/2004 |
| WO | WO 2004/099242 A2 | 11/2004 |
| WO | WO 2005/028618 A2 | 3/2005 |
| WO | WO 2006/069200 A2 | 6/2006 |
| WO | WO 2007/018563 A2 | 2/2007 |

OTHER PUBLICATIONS

Lederman et al (Molecular Immunology 28:1171-1181, 1991).*
Powell et al ( "Vaccine Design—the subunit and adjuvant approach" (Edited by Powell, M. F. and Newman, M. J.; 1995, Pharmaceutical Biotechnology (Plenum Press, New York and London.*
Greenspan et al (Nature Biotechnology, 1999, 7:936-937).*
Holmes, Exp. Opin.Invest. Drugs, 2001, 10(3):511-519).*
Coffey, T. et al. "Recombinational exchanges at the capsular polysaccharide biosynthesis locus . . ." *Molecular Microbiology,* Jun. 1998, 27:73-83; EMBL Database Accession No. 054547 Sequence ID 054547. Sequence only.
Giffard, P.M. et al. "The ftf gene encoding the cell-bound fructosyltransferase of *Streptococcus salivarius* ATCC 25975 is preceded by an insertion sequence and followed by FUR1 and clpP homologues" *Journal of General Microbiology,* 1993, 139:913-920.
Giffard, P.M. et al. Sequence ID CLPP_STRSL, Jun. 1, 1994, EMBL Database Accession No. P36398.
Larsson, C. et al. "Experimental Vaccination Against Group B *Streptococcus,* an Encapsulated Bacterium, with Highly Purified Preparations of Cell Surface Proteins Rib and α" *Infection and Immunity,* Sep. 1996, 64(9):3518-3523.
Maurizi, M.R. et al. "Sequence and Structure of Clp P, the Proteolytic Component of the ATP-dependent Clp Protease of *Escherichia coli*" *The Journal of Biological Chemistry,* Jul. 1990, 265(21):12536-12545.
Tsukioka, Y. et al. "Biological Function of the dTDP-Rhamnose Synthesis Pathway in *Streptococcus mutans*" *Journal of Bacteriology,* Feb. 1997, 179(4):1126-1134.
Wastfelt, M. et al. "Identification of a Family of Streptococcal Surface Proteins with Extremely Repetitive Structure" *The Journal of Biological Chemistry,* Aug. 1996, 271(31):18892-18897.
Yuichi, T. et al., Sequence ID P95779, May 1, 1997, EMBL Database Accession No. P95779.
Ellis, R.W. "New Technologies for Making Vaccines" in Vaccines, Plotkin, S.A. and Mortimer, E.A., Eds., Chapter 29, pp. 568-575, published by W.B. Saunders Company (Philadelphia), 1988.
Rudinger et al. in "Peptide Hormones", edited by Parsons, J.A., University Park Press, Jun. 1976, p. 6.
Burgess et al. *J. Cell Biology,* 1990, 111:2129-2138.
Lazar et al. *Molecular and Cellular Biology,* 1988, 8(3):1247-1252.
Jobling et al. *Mol. Microbiol.,* 1991, 5(7):1755-1767.
U.S. Appl. No. 10/799,072, filed Mar. 12, 2004, Hughes et al.
Ichiman, Y. and Yoshida, K. "Passive protection by human sera in mice against challenge with strains of group B streptococci" *Med. Microbiol. Immunol.,* 1986, 175:355-362.
Kunst, F. et al. "The complete genome sequence of the gram-positive bacterium *Bacillus subtilis*" *Nature,* 1997, 390(6657):249-256; sequence information: EMBL Database Accession No. Z99120.
Rodewald, A. et al. "Neonatal mouse model of Group B streptococcal infection" *J. Infectious Dis.,* 1992, 166:635-639.
Johri, A.K., et al. "Transcriptional and Proteomic Profiles of Group B *Streptococcus* Type V Reveal Potential Adherence Proteins Associated with High-level Invasion" *Infect. Immun.* 75:1473-1483, American Society for Microbiology (2007).
Maione D., et al. "Identification of a Universal Group B *Streptococcus* Vaccine by Multiple Genome Screen" *Science* 309(5731):148-150, American Association for the Advancement of Science (2005).
NCBI Database GenBank Report, Accession No. AAN00795, Tettelin et al. (Aug. 2002).
NCBI Database GenBank Report, Accession No. EA070329, Tettelin et al. (Oct. 2005).
Co-pending U.S. Appl. No. 11/892,024, inventor Hughes, et al., filed Aug. 17, 2007 (Not Published).
Co-pending U.S. Appl. No. 11/892,019, inventor Hughes, et al., filed Aug. 17, 2007 (Not Published).
U.S. Appl. No. 11/892,013, inventors Hughes et al., filed Aug. 17, 2007 (Not Yet Published).
Davis, B.D., et al., "Regulation of Gene Function," in *Microbiology* $3^{rd}$ *Edition,* Harper & Row Publishers, Inc., Hagerstown, Maryland (1980), pp. 263-267.
Harlow, E. and Lane, D., "Antibody-Antigen Interaction," in Chapter 3 of *Antibodies: A Laboratory Manual,* Cold Spring Harbor Laboratory Press, Cold Spring Harbor, New York (1988), pp. 23-25, 27-33, 76.
Herbert, W.J., et al., *Dictionary of Immunology $4^{th}$ Edition,* Academic Press Limited, San Diego, California (1995), pp. 58-59.
Greenbaum, J.A., et al., "Towards a consensus on datasets and evaluation metrics for developing B-cell epitope prediction tools," *J. Mol. Recognit.* 20:75-82, John Wiley & Sons, Ltd. (2007).
Greenspan, N.S. and Cera, E.D., "Defining epitopes: It's not as easy as it seems," *Nature Biotechnology* 17:936-937, Nature America Inc. (1999).
Hughes, M.J.G., et al., "Identification of Major Outer Surface Proteins of *Streptococcus agalacitae,*" *Infect. Immun.* 70:1254-1259, American Society for Microbiology (Mar. 2002).
Moore, J.C., et al., "Age-dependent presence of antibodies in rat dams, capable of conferring protection against B *Streptococcus* infection in neonates," *FEMS Microbiol. Letts.* 202:125-127, Elsevier Science B.V. (Jul. 2001).
Johri, A.K., et al., "Genetic manipulations of microorganisms for the degradation of hexachlorocyclohexane," *FEMS Microbiol Rev.* 19:69-84, Elsevier B.V. (1996).
Kolberg, J. and Sletten, K., "Monoclonal Antibodies That Recognize a Common Pneumococcal Protein with Similarities to Streptococcal Group A Surface Glyceraldehyde-3-Phosphate Dehydrogenase," *Infect. Immun.* 64:3544-3547, American Society for Microbiology (1996).
McGuinness, B.T., et al., "Class 1 outer membrane protein of *Neisseria meningitidis*: epitope analysis of the antigenic diversity between strains, implications for subtype definition and molecular epidemiology," *Mol. Microbiol.* 7:505-514, Blackwell Scientific Publications (1993).
McGuinness, B.T., et al., "Point mutation in meningococcal *por A* gene associated with increased endemic disease," *The Lancet* 337:514-517, Lancet Publishing Group (1991).
NCBI Database GenBank Report, Accession No. L38521, Boyd, D.A., et al., "*Streptococcus mutans* non-phosphorylating NADP-dependant glyceraldehyde-3-phosphate dehydrogenase (gapN) gene, complete cds," (Feb. 1995).
NCBI Database GenBank Report, Accession No. U34626, Habenicht, A., et al., "*Nicotiana plumbaginifolia* non-phosphorylating glyceraldehyde dehydrogenase (GapN) mRNA, complete cds," (Feb. 1997).
Rodewald, A., et al., "Neonatal mouse model of Group B streptococcal infection," *J. Infectious Dis.* 166:635-639, University of Chicago Press (1992).
Seifert, K.N., et al., "Characterization of group B streptococcal glyceraldehyde-3-phosphate dehydrogenase: surface localization, enzymatic activity, and protein-protein interactions." *Canadian Journal of Microbiology* 49:350-356, NRC Research Press (2003).
Stedman's Medical Dictionary, http://216.251.232.159/semdweb/internetsomd/ASP/1542968.asp, 1 page, accessed on Mar. 30, 2006.
Tricot, C., et al., "Evolutionary relationships among bacterial Carbamoyltransferases," Journal of General Microbiology 135:2453-2464, Society For General Microbiology (1989).
Ullberg, M., et al., "New receptor for human plasminogen on gram positive cocci." *APMIS: Acta Pathologica, Microbiologica, et Immunologica Scandinavica* 97:996-1002, Scandinavian Societies for Medical Microbiology and Pathology (1989).
International Preliminary Examination Report for International Application No. PCT/GB99/04376, filed Dec. 22, 1999, European Patent Office.

European Search Report for European Application No. EP 99 96 2421, mailed on Sep. 18, 2003, European Patent Office, The Hague.

European Search Report for European Application No. EP 05 00 9397, mailed on Aug. 16, 2005, European Patent Office, The Hague.

Partial European Search Report for European Application No. EP 05 00 9397, mailed on Aug. 16, 2005, European Patent Office, The Hague.

International Search Report for International Application No. PCT/GB99/04376, European Patent Office, mailed on May 15, 2000.

International Preliminary Examination Report for International Application No. PCT/GB02/01089, completed on Feb. 10, 2003, European Patent Office, Berlin-Germany.

International Search Report for International Application No. PCT/GB02/01089, mailed on Aug. 16, 2002, European Patent Office, Rijswijk, Netherlands.

International Search Report for International Application No. PCT/GB99/04377, mailed on Jul. 13, 2000, European Patent Office, Rijswijk, Netherlands.

International Preliminary Examination Report for International Application No. PCT/GB99/04377, completed on Mar. 22, 2001.

U.S. Appl. No. 10/799,072, inventors Hughes, M.J.G., filed Mar. 12, 2004 (Not Published).

Boyd, D.A., et al., "Sequence, expression, and function of the gene for the nonphosphorylating, NADP-dependent glyceraldehyde-3-phosphate dehydrogenase of *Streptococcus mutans*," *J. Bacteriol.* 177:2622-2727, American Society for Microbiology (1995).

Brown, A.T. and Wittenberger, C.L., "The Occurrence of Multiple Glyceraldehyde-3-Phosphate Dehydrogenases in Cariogenic Streptococci," *Biochem. Biophys. Res. Comm. 43*:217-224, Elsevier Science Ltd. (1971).

EMBL Database Accession No. Z99120, Kunst, F., et al., "The complete genome sequence of the gram-positive bacterium *Bacillus subtilis*," Nature 390(6657):249-256, Nov. 20, 1997 (Sequence Only).

Feng, S., et al., "P55, an Immunogenic but Nonprotective 55-Kilodalton *Borrelia burgdorferi* Protein in Murine Lyme Disease," *Infect. Immun. 64*:363-365, American Society for Microbiology (1996).

Gase, K., et al., "Cloning, sequencing and functional overexpression of the *Streptococcus equisimilis* H46A gapC gene encoding a glyceraldehyde-3-phosphate dehydrogenase that also functions as a plasmin(ogen)-binding protein," *Euro. J. Biochem.* 239:42-51, Blackwell Publishing (1996).

Habenicht, A., et al., "Sequence of the non-phosphorylating glyceraldehyde-3-phosphate dehydrogenase from *Nicotiana plumbaginifolia* and phylogenetic origin of the gene family" *Gene*, 198: 237-243, Elsevier Science B.V. (Feb. 1997).

Hassett, D.E., et al., "Neonatal DNA Immunization wit a Plasmid Encoding an Internal Viral Protein Is Effective in the Presence of Maternal Antibodies and Protects against Subsequent Viral Challenge," *J. Virol. 71*:7881-7888, American Society for Microbiology (1997).

Houghten, R.A., et al., "Relative Importance of Position and Individual Amino Acid Residues in Peptide Antigen-Antibody Interaction: Implications in the Mechanism of Antigenic Drift and Antigenic Shift," *Vaccines 86*:21-25, Cold Spring Harbor Laboratory (1986).

Ichiman, Y. and Yoshida, K., "Cross protection in mice with the Smith diffuse strain of *Staphyloccus aureus* versus a type Ia strain of group B streptococci," *Can. J. Microbiol. 28*:726-732, National Research Council of Canada (1982).

Itoh, T., et al., "Protective Efficacy against Group B Streptococcal Infection in Neonatal Mice Delivered from Preimmunized Pregnants," *Microbiol. Immunol. 30*:297-305, Japanese Society For Bacteriology (1986).

Lederman, S., et al., "A Single Amino Acid Substitution In a Common African Allele of the CD4 Molecule Ablates Binding of the Monoclonal Antibody, OKT4," *Mol. Immunol. 28*:1171-1181, Pregamon Press plc (1991).

Li, C.H., et al., "β-Endorphin omission analogs: Dissociation of immuoreactivity from other biological activities," *Proc. Natl. Acad. Sci. USA 77*:3211-3214, National Academy of Sciences (1980).

Skolnick, J., and Fetrow, J.S., "From genes to protein structure and function: novel applications of computational approaches in the genomic era," *Trends Biotechnol. 18*:34-39, Elsevier Science Publishers (1983).

* cited by examiner

SEQUENCE LISTING

<160> NUMBER OF SEQ ID NOS: 2

<210> SEQ ID NO 1
<211> LENGTH: 1146
<212> TYPE: DNA
<213> ORGANISM: group B streptococcus
<220> FEATURE:
<221> NAME/KEY: CDS
<222> LOCATION: (1)..(1146)
<223> OTHER INFORMATION:

<400> SEQUENCE: 1

```
atg ggc caa gaa cct atc atc gaa tat caa aat atc aat aaa gtg tat      48
Met Gly Gln Glu Pro Ile Ile Glu Tyr Gln Asn Ile Asn Lys Val Tyr
1               5                   10                  15 ggg gaa aat gtt gcg gtt gaa gat att aac ctt aaa att tac cct ggt      96
Gly Glu Asn Val Ala Val Glu Asp Ile Asn Leu Lys Ile Tyr Pro Gly
                20                  25                  30 gat ttc gtt tgt ttc atc ggt acg agt gga tca ggt aaa aca aca tta     144
Asp Phe Val Cys Phe Ile Gly Thr Ser Gly Ser Gly Lys Thr Thr Leu
            35                  40                  45 atg cgt atg gtt aac cat atg tta aaa cca aca aat ggt act cta tta     192
Met Arg Met Val Asn His Met Leu Lys Pro Thr Asn Gly Thr Leu Leu
50                  55                  60 ttt aag gga aaa gat att tct act att aac ccc att gaa tta aga cgc     240
Phe Lys Gly Lys Asp Ile Ser Thr Ile Asn Pro Ile Glu Leu Arg Arg
65                  70                  75                  80 aga att gga tat gtt atc caa aac att ggt tta atg cct cat atg acc     288
Arg Ile Gly Tyr Val Ile Gln Asn Ile Gly Leu Met Pro His Met Thr
                85                  90                  95 att tac gaa aat ata gtt ctt gta cca aaa tta ttg aaa tgg tca gaa     336
Ile Tyr Glu Asn Ile Val Leu Val Pro Lys Leu Leu Lys Trp Ser Glu
            100                 105                 110 gaa gct aaa aga gct aaa gca agg gaa ctt att aaa tta gtt gaa tta     384
Glu Ala Lys Arg Ala Lys Ala Arg Glu Leu Ile Lys Leu Val Glu Leu
        115                 120                 125 ccc gaa gaa tat ttg gat cgc tac cct agt gag ttg tct ggc ggt cag     432
Pro Glu Glu Tyr Leu Asp Arg Tyr Pro Ser Glu Leu Ser Gly Gly Gln
    130                 135                 140 caa caa cgt atc ggt gtc att cgc gct ctt gca gca gac caa gat att     480
Gln Gln Arg Ile Gly Val Ile Arg Ala Leu Ala Ala Asp Gln Asp Ile
145                 150                 155                 160 att tta atg gat gag cct ttt gga gct ctg gat cct att act aga gaa     528
Ile Leu Met Asp Glu Pro Phe Gly Ala Leu Asp Pro Ile Thr Arg Glu
                165                 170                 175 ggt att caa gac tta gtc aag tct ctt cag gaa gaa atg ggg aaa act     576
Gly Ile Gln Asp Leu Val Lys Ser Leu Gln Glu Glu Met Gly Lys Thr
```

-continued

```
                         180                 185                 190
atc atc tta gtt act cat gat atg gat gaa gcc ctc aag tta gca aca      624
Ile Ile Leu Val Thr His Asp Met Asp Glu Ala Leu Lys Leu Ala Thr
        195                 200                 205 aaa att att gtt atg gac aat ggt aaa atg gtc caa gaa ggg aca ccc      672
Lys Ile Ile Val Met Asp Asn Gly Lys Met Val Gln Glu Gly Thr Pro
    210                 215                 220 aat gat ctc tta cat cat cct gct acc agt ttc gtt gaa caa atg att      720
Asn Asp Leu Leu His His Pro Ala Thr Ser Phe Val Glu Gln Met Ile
225                 230                 235                 240 ggg gaa gag cgt ctt ctt cat gcg cag gct gat att acc cct gtt aaa      768
Gly Glu Glu Arg Leu Leu His Ala Gln Ala Asp Ile Thr Pro Val Lys
                245                 250                 255 cag ata atg tta aat aat cct gtt tca ata act gct gaa aaa aca cta      816
Gln Ile Met Leu Asn Asn Pro Val Ser Ile Thr Ala Glu Lys Thr Leu
            260                 265                 270 act gaa gct att aca cta atg cgc caa aaa cgc gtt gac tca ctt cta      864
Thr Glu Ala Ile Thr Leu Met Arg Gln Lys Arg Val Asp Ser Leu Leu
        275                 280                 285 gta acc gat aac ggt aaa tta att ggt ttt att gac tta gaa tct cta      912
Val Thr Asp Asn Gly Lys Leu Ile Gly Phe Ile Asp Leu Glu Ser Leu
    290                 295                 300 agc agt aaa tat aag aaa gay cga ctt gtt tct gat atc tta aaa cat      960
Ser Ser Lys Tyr Lys Lys Asp Arg Leu Val Ser Asp Ile Leu Lys His
305                 310                 315                 320 act gat ttt tat gtt atg gaa gac gac tta ctt aga aat act gct gag     1008
Thr Asp Phe Tyr Val Met Glu Asp Asp Leu Leu Arg Asn Thr Ala Glu
                325                 330                 335 cgt att tta aaa cgt ggt tta aaa tac gct cca gtt gtt gac cat gag     1056
Arg Ile Leu Lys Arg Gly Leu Lys Tyr Ala Pro Val Val Asp His Glu
            340                 345                 350 aat aac yta aag ggc att gtt act cgt gca tcc cta gtt gat atg tta     1104
Asn Asn Xaa Lys Gly Ile Val Thr Arg Ala Ser Leu Val Asp Met Leu
        355                 360                 365 tac gat att att tgg ggc gat act gaa acg gag gat caa taa             1146
Tyr Asp Ile Ile Trp Gly Asp Thr Glu Thr Glu Asp Gln
    370                 375                 380

<210> SEQ ID NO 2
<211> LENGTH: 381
<212> TYPE: PRT
<213> ORGANISM: group B streptococcus
<220> FEATURE:
<221> NAME/KEY: misc_feature
<222> LOCATION: (355)..(355)
<223> OTHER INFORMATION: The 'Xaa' at location 355 stands for Leu.

<400> SEQUENCE: 2

Met Gly Gln Glu Pro Ile Ile Glu Tyr Gln Asn Ile Asn Lys Val Tyr
1               5                   10                  15

Gly Glu Asn Val Ala Val Glu Asp Ile Asn Leu Lys Ile Tyr Pro Gly
                20                  25                  30

Asp Phe Val Cys Phe Ile Gly Thr Ser Gly Ser Gly Lys Thr Thr Leu
            35                  40                  45

Met Arg Met Val Asn His Met Leu Lys Pro Thr Asn Gly Thr Leu Leu
        50                  55                  60

Phe Lys Gly Lys Asp Ile Ser Thr Ile Asn Pro Ile Glu Leu Arg Arg
65                  70                  75                  80

Arg Ile Gly Tyr Val Ile Gln Asn Ile Gly Leu Met Pro His Met Thr
                85                  90                  95
```

-continued

```
Ile Tyr Glu Asn Ile Val Leu Val Pro Lys Leu Leu Lys Trp Ser Glu
            100                 105                 110

Glu Ala Lys Arg Ala Lys Ala Arg Glu Leu Ile Lys Leu Val Glu Leu
            115                 120                 125

Pro Glu Glu Tyr Leu Asp Arg Tyr Pro Ser Glu Leu Ser Gly Gly Gln
            130                 135                 140

Gln Gln Arg Ile Gly Val Ile Arg Ala Leu Ala Ala Asp Gln Asp Ile
145                 150                 155                 160

Ile Leu Met Asp Glu Pro Phe Gly Ala Leu Asp Pro Ile Thr Arg Glu
                165                 170                 175

Gly Ile Gln Asp Leu Val Lys Ser Leu Gln Glu Glu Met Gly Lys Thr
                180                 185                 190

Ile Ile Leu Val Thr His Asp Met Asp Glu Ala Leu Lys Leu Ala Thr
            195                 200                 205

Lys Ile Ile Val Met Asp Asn Gly Lys Met Val Gln Glu Gly Thr Pro
210                 215                 220

Asn Asp Leu Leu His His Pro Ala Thr Ser Phe Val Glu Gln Met Ile
225                 230                 235                 240

Gly Glu Glu Arg Leu Leu His Ala Gln Ala Asp Ile Thr Pro Val Lys
                245                 250                 255

Gln Ile Met Leu Asn Asn Pro Val Ser Ile Thr Ala Glu Lys Thr Leu
                260                 265                 270

Thr Glu Ala Ile Thr Leu Met Arg Gln Lys Arg Val Asp Ser Leu Leu
            275                 280                 285

Val Thr Asp Asn Gly Lys Leu Ile Gly Phe Ile Asp Leu Glu Ser Leu
            290                 295                 300

Ser Ser Lys Tyr Lys Lys Asp Arg Leu Val Ser Asp Ile Leu Lys His
305                 310                 315                 320

Thr Asp Phe Tyr Val Met Glu Asp Asp Leu Leu Arg Asn Thr Ala Glu
                325                 330                 335

Arg Ile Leu Lys Arg Gly Leu Lys Tyr Ala Pro Val Val Asp His Glu
                340                 345                 350

Asn Asn Xaa Lys Gly Ile Val Thr Arg Ala Ser Leu Val Asp Met Leu
            355                 360                 365

Tyr Asp Ile Ile Trp Gly Asp Thr Glu Thr Glu Asp Gln
            370                 375                 380
```

GENES AND PROTEINS, AND THEIR USE

REFERENCE TO RELATED APPLICATION

This application is a continuation of U.S. application Ser. No. 10/096,162, filed Mar. 11, 2002 and issued on May 10, 2005 as U.S. Pat. No. 6,890,539, which claims priority to U.K. Publication No. GB0105922D under 35 U.S.C. §365, filed Mar. 09, 2001 and is a continuation-in-part of U.S. application Ser. No. 09/868,352, filed Sep. 10, 2001 under 35 U.S.C. §371(c) and issued on Nov. 02, 2004 as U.S. Pat. No. 6,812,021, which is the national stage filing of International Application No. PCT/GB99/04377, filed Dec. 22, 1999, each of which is hereby incorporated by reference herein in its entirety, including any figures, tables, nucleic acid sequences, amino acid sequences, and drawings.

FIELD OF THE INVENTION

This invention relates to the identification of a bacterial gene and protein, and its use. More particularly, it relates to its use in therapy, for immunisation and in screening for drugs.

BACKGROUND TO THE INVENTION

Group B *Streptococcus* (GBS), also known as *Streptococcus agalactiae*, is the causative agent of various conditions. In particular, GBS causes:

Early Onset Neonatal Infection.

This infection usually begins in utero and causes severe septicaemia and pneumonia in infants, which is lethal if untreated and even with treatment is associated with a 10-20% mortality rate.

Late Onset Neonatal Infection.

This infection occurs in the period shortly after birth until about 3 months of age. It causes a septicaemia, which is complicated by meningitis in 90% of cases. Other focal infections also occur including osteomyelitis, septic arthritis, abscesses and endopthalmitis.

Adult Infections.

These appear to be increasingly common and occur most frequently in women who have just delivered a baby, the elderly and the immunocompromised. They are characterised by septicaemia and focal infections including osteomyelitis, septic arthritis, abscesses and endopthalmitis.

Urinary Tract Infections.

GBS is a cause of urinary tract infections and in pregnancy accounts for about 10% of all infections.

Veterinary Infections.

GBS causes chronic mastitis in cows. This, in turn, leads to reduced milk production and is therefore of considerable economic importance.

GBS infections can be treated with antibiotics. However, immunisation is preferable. It is therefore desirable to develop an immunogen that could be used in a therapeutically-effective vaccine.

SUMMARY OF THE INVENTION

The present invention is based on the identification of a gene in GBS, and also related organisms, the product of which may be localised on the outer surface of the organism and therefore may be used as a target for immuno-therapy.

According to one aspect of the invention, a peptide is encoded by a gene identified herein as pho2-2, obtainable from Group B *Streptococcus*, or a homologue or functional fragment thereof. Such a peptide is suitable for therapeutic use, e.g. when isolated.

The term "functional fragment" is used herein to define a part of the gene or peptide which retains the activity of the whole gene or peptide. For example, a functional fragment of the peptide may be used as an antigenic determinant, useful in a vaccine or in the production of antibodies.

A gene fragment may be used to encode the active peptide. Alternatively, the gene fragment may have utility in gene therapy, targetting the wild-type gene in vivo to exert a therapeutic effect.

A peptide according to the present invention may comprise the amino acid sequence identified herein as SEQ ID NO. 2, or a functional fragment thereof.

Because of the extracellular or cell surface location, the peptide of the present invention may be a suitable candidate for the production of therapeutically-effective vaccines against GBS. The term "therapeutically-effective" is intended to include the prophylactic effect of vaccines. For example, a vaccine may comprise a peptide according to the invention, or the means for its expression, for the treatment of infection. The vaccine may be administered to females prior to or during pregnancy to protect mother and neonate against infection by GBS.

According to another aspect of the invention, the peptide or gene may be used for screening potential antimicrobial drugs or for the detection of virulence.

A further aspect of this invention is the use of any of the products identified herein, for the treatment or prevention of a condition associated with infection by a Group B Streptococcal strain.

Although the protein has been described for use in the treatment of patients, veterinary uses of the products of the invention are also considered to be within the scope of the present invention. In particular, the peptide or the vaccines may be used in the treatment of chronic mastitis, especially in cows.

DESCRIPTION OF THE DRAWINGS

The invention is described with reference to the accompanying drawing where.

DESCRIPTION OF THE INVENTION

Figure 1:
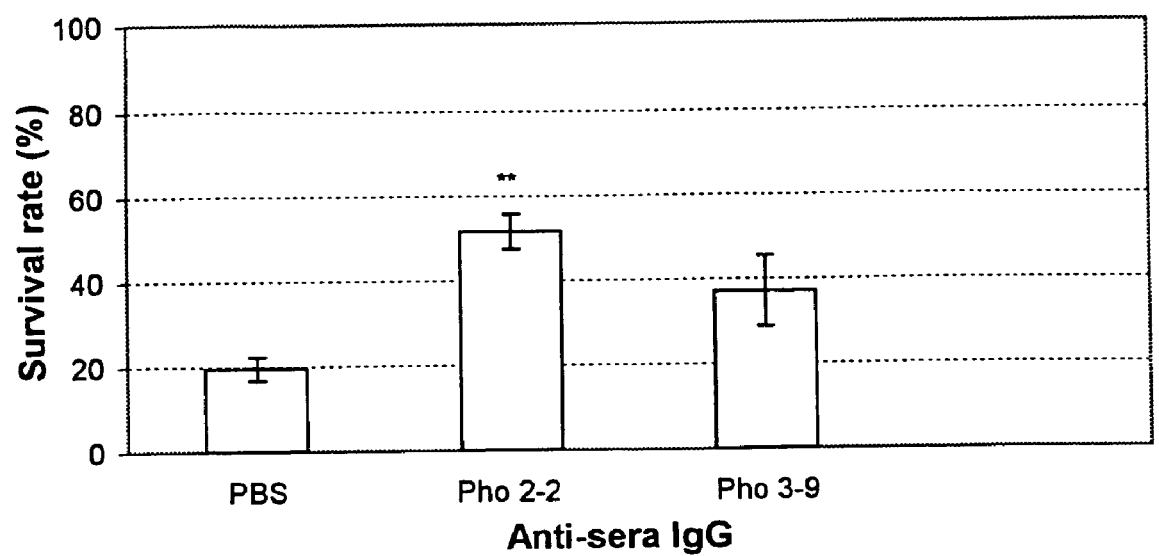
FIG. 1 is a graphic illustration of the average level of protection offered by anti-pho2-2 (SEQ ID NO:2) anti-sera against a challenge dose of GBS.

The present invention is described with reference to Group B Streptococcal strain M732. However, all the GBS strains and many other bacterial strains are likely to include related peptides or proteins having amino acid sequence homology with the peptide of M732. Organisms likely to contain the peptide include, but are not limited to, *S. pneumoniae, S. pyogenes, S. suis, S. milleri*, Group C and Group G *Streptococci* and *Enterococci*. Vaccines to each of these may be developed in the same way as described for GBS.

Preferably, the peptides that may be useful for the production of vaccines have greater than 40% sequence similarity with the peptide identified herein. More preferably, the peptides have greater than 60% sequence similarity. Most preferably, the peptides have greater than 80% sequence similarity, e.g. 95% similarity. With regard to the polynucleotide sequence identified herein, related polynucleotides that may be useful in the various aspects of the invention may have greater than 40% identity with the sequence identified herein. More preferably, the polynucleotide sequences have greater than 60% sequence identity. Most preferably, the polynucleotide sequences have greater than 80% sequence identity, e.g. 95% identity.

The terms "similarity" and "identity" are known in the art. The use of the term "identity" refers to a sequence comparison based on identical matches between correspondingly identical positions in the sequences being compared. The term "similarity" refers to a comparison between amino acid sequences, and takes into account not only identical amino acids in corresponding positions, but also functionally similar amino acids in corresponding positions. Thus similarity between polypeptide sequences indicates functional similarity, in addition to sequence similarity.

Levels of identity between gene sequences and levels of identity or similarity between amino acid sequences can be calculated using known methods. In relation to the present invention, publicly available computer based methods for determining identity and similarity include one BLASTP, BLASTN and FASTA (Atschul et al., J. Molec. Biol., 1990; 215:403-410), the BLASTX program available from NCBI, and the Gap program from Genetics Computer Group, Madison Wis. The levels of similarity and identity provided herein, were obtained using the Gap program, with a Gap penalty of 12 and a Gap length penalty of 4 for determining the amino acid sequence comparisons, and a Gap penalty of 50 and a Gap length penalty of 3 for the polynucleotide sequence comparisons.

Having characterised a gene according to the invention, it is possible to use the gene sequence to establish homologies in other microorganisms. In this way it is possible to determine whether other microorganisms have similar outer surface products. Sequence homologies may be established by searching in existing databases, e.g. EMBL or Genbank.

A fragment of the gene sequence disclosed herein may be used to prepare a vaccine product, or as a probe in a diagnostic method, or to identify homologues in other microorganisms. Preferably the fragment will be at least 20 nucleic acids, more preferably at least 30 nucleic acids, and most preferably at least 70 nucleic acids.

When used to identify homologues, the gene sequence, or fragment thereof, will preferably hybridise to the putative homologue under stringent hybridisation conditions. Stringent hybridisation conditions are those described by Sambrook et al., Molecular Cloning, A Laboratory Manual, Cold Spring Harbor Laboratory Press (1989), 1.101-1.104. According to this, hybridisation under stringent conditions means that a positive hybridisation signal is still observed after washing for 1 hour with 1×SSC buffer and 0.1% SDS at 55° C., preferably at 62° C. and most preferably at 68° C.

Peptides or proteins according to the invention may be purified and isolated by methods known in the art. In particular, having identified the gene sequence, it will be possible to use recombinant techniques to express the genes in a suitable host. Active fragments and homologues can be identified and may be useful in therapy. For example, the peptide or its active fragments may be used as antigenic determinants in a vaccine, to elicit an immune response. They may also be used in the preparation of antibodies, for passive immunisation, or diagnostic applications. Peptide fragments may be used to identify those parts of the protein that have the most favourable antigenic epitopes. The fragments can be generated by methods known to those skilled in the art. For example, partial digests of the complete protein can be made and tested. Alternatively, synthetic peptide fragments can be made and tested.

The fragments may be tested to establish which fragments elicit the strongest immune response.

A therapeutic antibody of the invention will have affinity for the protein (or peptide) of the invention and preferably should not cross-react with unrelated proteins or proteins in the patient.

Suitable antibodies which may be active against the peptide of the invention, include monoclonal antibodies, or fragments thereof, including single chain fv fragments. Methods for the preparation of antibodies will be apparent to those skilled in the art.

The preparation of vaccines is known to those skilled in the art. Vaccine compositions can be formulated with suitable carriers or adjuvants, e.g. alum, as necessary or desired, and used in therapy, to provide effective immunisation against Group B *Streptococci* or other microorganisms that contain related proteins. The preparation of vaccine formulations will be apparent to the skilled person.

More generally, and as is well known to those skilled in the art, a suitable amount of an active component of the invention can be selected, for therapeutic use, as can suitable carriers or excipients, and routes of administration. These factors will be chosen or determined according to known criteria such as the nature/severity of the condition to be treated, the type or health of the subject etc.

The products of the invention may also be used in assays to screen potential antimicrobial drugs. For example, the protein of the invention may be used as a target for antimicrobial therapy, to localise a drug to the infecting microbe.

The products of the present invention were identified as follows:

A partial gene library of GBS (strain M732) chromosomal DNA was prepared using the plasmid vectors pFW-phoA1, pFW-phoA2 and pFW-phoA3 (Podbielski, A. et al. 1996. Gene 177:137-147). These plasmids possess a constitutive spectinomycin adenyltransferase antibiotic resistance marker, which confers a high level of spectinomycin resistance and is therefore easily selected. Furthermore, these vectors contain a truncated (leaderless) *Escherichia coli* phoA gene for alkaline phosphatase. The three vectors differ only with respect to the reading frame in which the leaderless phoA gene exists, as compared to an upstream in-frame BamHI restriction enzyme site. Because this truncated *E. coli* phoA gene lacks the appropriate leader sequence for export of this enzyme across the bacterial membrane, extracellular alkaline phosphatase activity is absent when these plasmids are propagated in an *E. coli* phoA mutant (e.g. strain DH5α). The chromogenic alkaline phosphatase substrate, XP (5-bromo-4-chloro-3-indolyl-phosphate), does not enter intact bacterial cells and therefore only exported or surface associated alkaline phosphatase activity can be detected. When exported or surface associated alkaline phosphatase activity is present, the chromogenic XP substrate is cleaved to yield a blue pigment and the corresponding bacterial colonies can be identified by their blue colour.

Plasmid DNA was digested to completion with BamHI and dephosphorylated using shrimp alkaline phosphatase. GBS genomic DNA was partially digested with Sau3AI, size fractionated on a sucrose gradient and fragments <1 kb in size were ligated into the prepared pFW-phoA vectors. *E. coli* strain DH5α was chosen as the cloning host since it lacks a functional phoA gene. Recombinant plasmids were selected on Luria agar containing 100 μg/ml of spectinomycin and 40 μg/ml of the chromogenic XP substrate. *E. coli* transformants harbouring plasmids containing GBS insert DNA that complements the export signal sequence of the leaderless phoA gene were identified by the blue colour of the colonies.

Approximately 30000 different recombinant plasmids containing GBS insert DNA were screened in this manner and 83 recombinant plasmids, which complemented the leaderless phoA, were chosen for further study.

From these experiments, several clones were selected each containing a plasmid containing a gene (or part thereof), which complemented the leaderless phoA.

A clone was selected containing a plasmid designated pho2-2. This plasmid contained a gene (or part thereof), which complemented the leaderless phoA. The nucleotide and deduced amino acid sequences of the gene are shown as SEQ ID NOS. 1 and 2, respectively.

A comparison of the amino acid sequence of pho2-2 was performed.

Homologues to the GBS pho2-2 gene product can be identified in *Enterococcus faecalis*, *Escherichia coli* (malK and afuC), *Bacillus subtilis* (glnO), *Haemophilus influenzae* (yebM and potA), *Streptococcus pyogenes*, *Streptococcus pneumoniae* and *Salmonella typhimurium* (malK). The *E. faecalis*, *S. pyogenes* and *S. pneumoniae* homologues were identified from genome sequence data and no annotations were available as to the identity of the gene or gene products. In all other cases, homologues represented ATP-binding transport proteins that are part of ABC type transporters. Many of the components of ABC type transporters are membrane or cell surface associated, as these systems are involved in the transport of macromolecules from the extracellular environment to the intracellular compartment.

Having identified the gene in each clone it is then possible to obtain the full-length gene sequence, as follows.

Using the identified and sequenced gene fragment, oligonucleotide primers were designed for genomic DNA sequencing. These primers were designed so as to sequence in an 'outward' direction from the obtained sequence. Once read, the sequence obtained was checked to see if the 5' and 3' termini of the gene had been reached. The presence of these features was identified by checking against homologous sequences, and for the 5' end the presence of an AUG start codon (or accepted equivalent) preceded by a Shine-Dalgarno consensus sequence, and for the 3' end, the presence of a translation termination (Stop) codon.

Upon identification of the full-length gene, primers were designed for amplification of full-length product. Primers used included restriction enzyme recognition sites (NcoI at the 5' end and EcoO109I at the 3' end) to allow subsequent cloning of the product into the Lactococcal expression system used.

PCR was carried out using the primers, and the products cloned into a pCR 2.1 cloning vector (Invitrogen). Following confirmation of the presence of the cloned fragment, the DNA was excised using the restriction enzymes NcoI and EcoO109I.

The vector into which this fragment was inserted was a modified version of pNZ8048 (Kuipers, O. P. et al. (1998) J. Biotech 64: 15-21). This vector, harbouring a lactococcal origin of replication, a chloramphenicol resistance marker, an inducible nisin promoter and a multicloning site was altered by the replacement of the multicloning site with two 10× His tags, flanked on the 5-most end with an NcoI site, split in the middle with a multicloning site (including an EcoO109I site), and a stop (termination) codon at the 3' end of the His tags.

The gene of interest was inserted so that a 10× His tag was in the 3' position relative to the coding region. Following transformation of the recombinant plasmid into *L. lactis* (strain NZ9000-Kuipers, O. P. et al. (1998) supra), a 400 ml liquid culture was set up and translation of the protein was induced by the addition of nisin to the culture. After a 2 hour incubation, the cells were harvested and lysed by bead beating. The resultant lysate was cleared by centrifugation, then passed over a metal affinity (Talon, Clonetech) column. The column was washed repeatedly before bound proteins were eluted with Imidazole.

To identify fractions containing the His-tagged recombinant protein, an aliquot from each fraction was analysed by SDS-PAGE, Western blotted and probed with anti-His antibodies.

The recombinant protein obtained was then used to immunise New Zealand white rabbits, with pre-immune sera being harvested prior to immunisation. Following a boost, the rabbits were sacrificed and sera collected. This sera was used in Western blots, ELISA and animal protection models.

Using the sera obtained from the animal studies, immunosorption studies were carried out.

Group B *Streptococcus* was grown in 20 ml Todd Hewitt broth (THB) for 8 hours, harvested and resuspended in 5 ml PBS. 50 µl aliquots of this were used to coat wells in a 96 well plate (Nunc Immuno-Sorb). This was left at 4° C. overnight to allow for adsorbance of the bacteria onto the plate. Plates were washed twice with PBS, then blocked with 3% BSA in PBS for 1hr at 37° C. Plates were again washed. Serial 10 fold dilutions of the sera were made in PBS and 50 µl of these dilutions were added to the wells of the plate, in duplicate. The plate was covered and incubated for 1 hr at 37° C. The plate was washed, then 50 µl anti-rabbit alkaline phosphatase conjugated secondary antibody at a concentration of 1:5000 was added to each well. Following incubation at 37° C. for an hour, the plate was washed again. 50 µl substrate (PNPP) was added to each well, and the reaction allowed to proceed for 30 min before the adsorbance was read at 405 nm.

The results showed that the antibody bound to the whole cells indicating that pho2-2 resides on the outer surface of the cell.

Animal protection studies were also carried out to test the effectiveness of protection on the immunised rabbits.

Anti-sera against the pho2-2 outer surface protein and a further protein (pho3-9) identified in the same screen were raised in rabbits and the IgG from each anti-sera was purified using Protein A column chromatography. Newborn pups from time-mated Sprague Dawley rats were 'immunised' with 50 µl of the purified IgG intraperitoneally and returned to different mothers for at least 5 hours before they were challenged with the GBS.

The A909 strain of GBS was used as the challenge. The strain was streaked on to a blood agar plate, and allowed to grow over the weekend at room temperature. A single colony of GBS was used to produce the inoculum in THB. Following overnight growth, the GBS bacteria were centrifuged, and an appropriate volume of PBS added to produce a final dilution of $1 \times 10^6$ CFU/ml GBS ($5 \times 10^4$ GBS/50 µl). The innoculum was kept on ice until use in the challenge assay in the rat pups.

The GBS was administered subcutaneously to each rat and the time of challenge recorded. All pups were monitored for approximately 63 hours after the GBS challenge.

Table A shows the percentage of pups that survived 63 hours after challenge with GBS. This data has been represented in a graph in FIG. 1.

TABLE A

| Study date | PBS | Pho 2-2 | Pho 3-9 |
|---|---|---|---|
| Feb. 27, 2001 | 14 | 52 | 41 21 |
| Mar. 27, 2001 | 20 | — | 67 53 |
| Apr. 3, 2001 | 17 | — | 46 — |
| MEAN | 19.50 | 51.50 | 37.00 |

TABLE A-continued

| Study date | PBS | Pho 2-2 | Pho 3-9 |
|---|---|---|---|
| SD | 5.57 | 11.27 | 22.63 |
| SE | 2.78 | 5.63 | 16.00 |

The pho2-2 protein offered significant protection against GBS infection compared to the PBS control and to the other outer surface protein pho3-9.

We claim:

1. A method of inducing an immune response against Group B *Streptococcus* comprising administering to a subject a composition comprising an isolated polypeptide, which comprises an amino acid sequence at least 95% identical to SEQ ID NO: 2, wherein said polypeptide is recognized by an antibody that specifically binds to a polypeptide consisting of SEQ ID NO: 2.

2. The method of claim 1, wherein said amino acid sequence is encoded by a polynucleotide comprising SEQ ID NO: 1.

3. The method of claim 1, wherein said polypeptide further comprises at least one heterologous polypeptide.

4. The method of claim 3, wherein said heterologous polypeptide is a His tag.

5. The method of claim 1, wherein said composition further comprises at least one carrier.

6. The method of claim 1, wherein said composition further comprises at least one adjuvant.

7. The method of claim 6, wherein said at least one adjuvant is alum.

8. The method of claim 1, wherein said subject is an animal.

9. The method of claim 8, wherein said animal is a human or a cow.

10. The method of claim 1, wherein said immune response further protects or treats a condition associated with Group B-*Streptococcal* infection.

11. The method of claim 10, wherein said condition is selected from the group consisting of: a Group B *Streptococcal* infection, septicemia, pneumonia, osteomyelitis, septic arthritis, abscesses, endophthalmitis, urinary tract infection, and chronic mastitis.

12. The method of claim 11, wherein said condition is a Group B *Streptococcal* infection.

13. The method of claim 11, wherein said condition is a urinary tract infection.

14. The method of claim 1, wherein said polypeptide comprises SEQ ID NO: 2.

15. The method of claim 10, wherein said immune response protects or treats a neonate.

16. The method of claim 1, wherein said immune response is an antibody response.

* * * * *

UNITED STATES PATENT AND TRADEMARK OFFICE
CERTIFICATE OF CORRECTION

| | | |
|---|---|---|
| PATENT NO. | : 7,592,011 B2 | Page 1 of 1 |
| APPLICATION NO. | : 10/944521 | |
| DATED | : September 22, 2009 | |
| INVENTOR(S) | : Hughes et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 362 days Delete the phrase "by 362 days" and insert -- by 598 days --

Signed and Sealed this

Thirteenth Day of April, 2010

David J. Kappos
*Director of the United States Patent and Trademark Office*